United States Patent [19]

Umetani et al.

[11] Patent Number: 4,890,310

[45] Date of Patent: Dec. 26, 1989

[54] SPECTRAL TYPE RADIATION IMAGING SYSTEM

[75] Inventors: Keiji Umetani, Fuchu; Ken Ueda, Ome; Ryuichi Suzuki, Kokubunji; Hisatake Yokouchi, Tokyo, all of Japan

[73] Assignee: Hitachi, Ltd., Tokyo, Japan

[21] Appl. No.: 106,345

[22] Filed: Oct. 9, 1987

[30] Foreign Application Priority Data

Oct. 9, 1986 [JP] Japan .................................. 61-239008

[51] Int. Cl.⁴ .............................................. G01T 1/36
[52] U.S. Cl. ...................................... 378/82; 378/62; 378/99
[58] Field of Search .................... 378/99, 98, 5, 62, 82; 358/111

[56] References Cited

U.S. PATENT DOCUMENTS

| 3,974,386 | 8/1976 | Mistretta et al. | 378/99 |
| 4,432,370 | 2/1984 | Hughes et al. | |
| 4,445,226 | 4/1984 | Brody | 378/99 |
| 4,511,799 | 4/1985 | Bjorkholm | 378/5 |
| 4,544,949 | 10/1985 | Kurihara | 358/111 |
| 4,709,382 | 11/1987 | Sones | 378/5 |

Primary Examiner—Carolyn E. Fields
Assistant Examiner—David P. Porta
Attorney, Agent, or Firm—Antonelli, Terry & Wands

[57] ABSTRACT

An x-ray having the energy bandwidth which extends between above and below the absorption edge energy of an element constituting a contrast agent is emitted from an x-ray source as an x-ray to be projected to an object, the x-ray at the higher energy component than the absorption energy of the contrast-agent constituting element is detected by one x-ray detector, the x-ray, having been transmitted through the one x-ray detector, at the lower energy component than the absorption edge energy of the contrast agent constituting element is detected by another x-ray detector, and a subtraction image is obtained by processing the image data from both detectors.

14 Claims, 3 Drawing Sheets

SPECTRAL TYPE RADIATION IMAGING SYSTEM

BACKGROUND OF THE INVENTION

This invention relates to x-ray imaging or x-raying using contrast agent, and more particularly to an imaging system which can preferably adopt an energy subtraction technique for imaging.

One example of the devices of obtaining a subtraction image between two images taken at different x-ray energy spectra is disclosed in U.S. Pat. No. 4,445,226 to William R. Brody. This prior art discloses the following two imaging techniques. (1) X-rays with different energy spectra are provided through the filtration of a broad-energy bandwidth x-ray emitted from an x-ray tube using two different filters. By rapidly exchanging these filters, images with different energy spectra are sequentially taken. (2). A broad-energy bandwidth x-ray emitted from the x-ray tube is used as x-ray source. The x-ray images are simultaneously taken using an energy-sensitive detector. Some data processing between the images with different energy spectra obtained in the manner of (1) or (2) provides an objective subtraction image.

The configuration in the manner of (2) is advantageous in that it provides an accurate subtraction image even if an object is moving. The energy-sensitive detector disclosed in the above reference consists of an array of two kinds of scintillators stacked at the front and back part thereof; the scintillators in the front part detect the lower energy x-rays while the scintillators in the back part detect the higher energy x-rays which have passed the front part of the detector. Such a configuration, however, cannot provide a sufficient resolution of energy spectra. More specifically, as proposed in U.S. Pat. No. 4,432,370 to E. Barrie Hughes et al, if iodine is introduced as a contrast agent into a body to be examined (e.g. vein), and two imagings are carried out using monochromatic x-rays at the energies slightly above and below the K-absorption edge of iodine so as to obtain a subtraction image, unnecessary tissue images are cancelled out to provide a clear contrast of the image. In order to successfully achieve this, however, a detector having such a resolution as permitting very adjacent two spectra to be separated and detected is required. It was difficult to obtain a satisfactory result by using the energy-sensitive detector disclosed in U.S. Pat. No. 4,445,226 in the method of U.S. Pat. No. 4,432,370.

SUMMARY OF THE INVENTION

An object of this invention is to provide a spectral x-ray imaging system which can separate images by x-rays at very adjacent two energies and simultaneously image them.

In order to achieve the above object, in accordance with this invention, there is used, as an x-ray to be projected to a subject, a quasi-monochromatic x-ray the energy bandwidth of which extends over the region slightly above and below the absorption edge energy of the element constituting a contrast agent. Also, the detector used has only to be sensitive to the variation of energy in the region just above and below the absorption edge of the contrast agent constituting element and to be able to detect the x-rays individually at the energies in that region (hereinafter such a detector is referred to as an energy-sensitive detector). More specifically, this detector consists of a front and back part, the higher energy x-ray primarily detected by a scintillator arranged in the front part which is made of the compound containing the contrast agent constituting element while the lower energy x-rays which have passed above scintillator are primarily detected by another scintillator arranged in the back part. In accordance with such a configuration, the x-rays at the energies just above and below the absorption edge of the contrast agent constituting element can be separately detected and thus an energy subtraction image free from any motion artifacts can be achieved.

DESCRIPTION OF THE PREFERRED EMBODIMENTS

Figure 1:
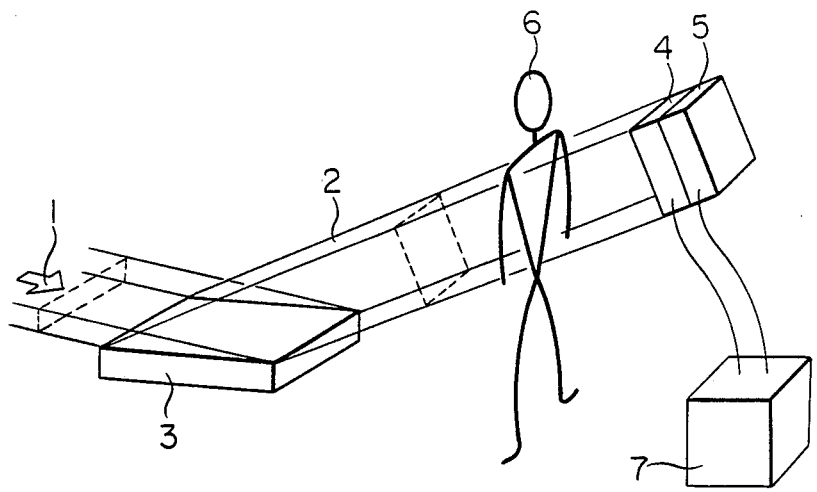
FIG. 1 is a block diagram of one embodiment according to this invention.

Now referring to FIG. 1, one embodiment will be explained. A synchrotron radiation 1 is emitted from a high energy electron storage ring in the tangential direction of an electron orbit when high energy electrons are bent in their electron orbit by the magnetic field. The synchrotron radiation 1 has a high directivity so that it is emitted as a flat fan beam having a section intensity distribution which is wide in the electron orbit deflecting plane and narrow in the direction perpendicular to the plane. The synchrotron radiation 1 is spectroscopically separated by a spectroscope 3. The spectroscope 3, when it is an asymmetric reflection type spectroscope, provides a quasi-monochromatic x-ray 2 which has an energy bandwidth wider than in the normal symmetric reflection type spectroscope. Due to the asymmetric reflection, the quasi-monochromatic x-ray 2 will be a pyramidal beam the section of which can be extended vertically in FIG. 1 so as to permit the two-dimensional imaging thereof. The angle formed by the spectroscope 3 with the synchrotron radiation 1 is set to a specific value, and the center of the energy band of the quasi-monochromatic x-ray 2 is made coincident with the absorption edge energy of the element constituting a contrast agent. The quasi-monochromatic x-ray 2 under such a condition is projected onto an object 6. The xray having passed through the object is detected by an energy-sensitive detector in such a way that the image formed by the x-ray having higher energy than the absorption edge energy is detected by a higher energy detector 4 while the image formed by the x-ray having lower energy than the absorption edge energy is detected by a lower energy detector 5. These image data are processed by a data recording and reproducing processing device 7. Namely, the subtraction between the image data obtained by the detector 4 and the image data obtained by the detector 5 provides a subtraction image in which only the distribution of the contrast agent is emphasized.

Figure 2:
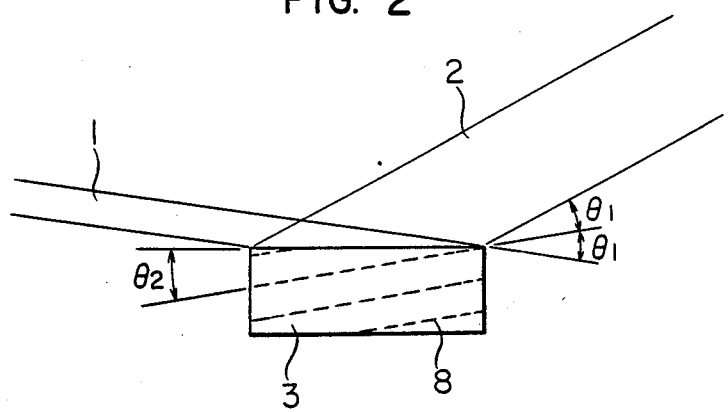
FIG. 2 is a sectional view of an element shown in FIG. 1.

Referring to FIG. 2, the spectroscope 3 will be explained. The spectroscope 3 is an asymmetric reflection type spectroscope, which is made of crystal such as silicon, germanium, quartz, etc. The structure thereof is such that crystal lattice plane 8 contributing to the x-ray diffraction form a gradient of angle $\theta_2$ with the crystal lattice plane. Here, the synchrotron radiation 1 is incident to the crystal lattice planes 8 at an angle $\theta_1$ and only the x-ray having the energy satisfying the Bragg diffraction condition diffracts at the angle of $\theta_1$. Thus, the synchrotron radiation 1 incident at an angle of $\theta_1 - \theta_2$ formed with the crystal surface diffracts at an angle of $\theta_1 + \theta_2$ formed with the crystal surface, thus providing the x-ray 2 with an extended beam width. In the case of asymmetrical reflection, the x-ray 2 will be a quasi-monochromatic x-ray in which the energy bandwidth of the diffracted x-ray is wider than in the case of symmetric reflection ($\theta_2 = 0$), which extends over the range very adjacent to the absorption edge energy of the contrast agent constituting element.

Figure 3:
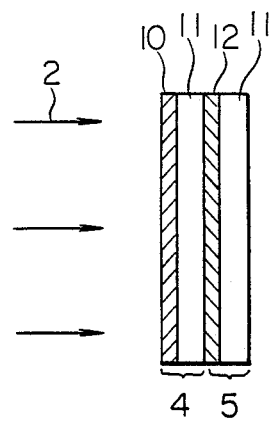
FIG. 3 is a sectional view of elements 4 and 5 shown in FIG. 1.

Referring to FIG. 3, the construction of the energy-sensitive detector will be explained. The quasi-monochromatic x-ray 2 having passed through the object is first incident to the higher energy detector 4. This higher energy detector 4 is constituted by a higher energy scintillator 10 and a photodetector 11. The higher energy scintillator 10 is made of, in its main component, the same material as the contrast agent constituting element or the element having a greater atomic number than it. For example, if the contrast agent is iodine, the scintillator made of an iodide compound such as cesium iodide, sodium iodide, etc. is used. If the contrast agent is barium, the scintillator made of a barium compound such as several kinds of barium halide, etc. These compounds selectively greatly absorb the x-ray at the higher energy than the energy at the absorption edge of the contrast agent constituting element. The absorbed x-ray energy is converted into fluorescence, which is detected by the photodetector 11 to provide an x-ray image. Next, the x-ray at the lower energy than the absorption edge energy of the contrast agent constituting element is substantially transmitted through the higher energy detector 4 and enters the lower energy detector 5. This detector 5 is constituted by a lower energy scintillator 12 and a photodetector 13. The lower energy scintillator 13 may be made of any suitable material since it absorbs only the x-ray having been transmitted through the higher energy detector 4. The absorbed x-ray energy is converted into fluorescence, which is detected by the photodetector 13 to provide an x-ray image.

Figure 4:
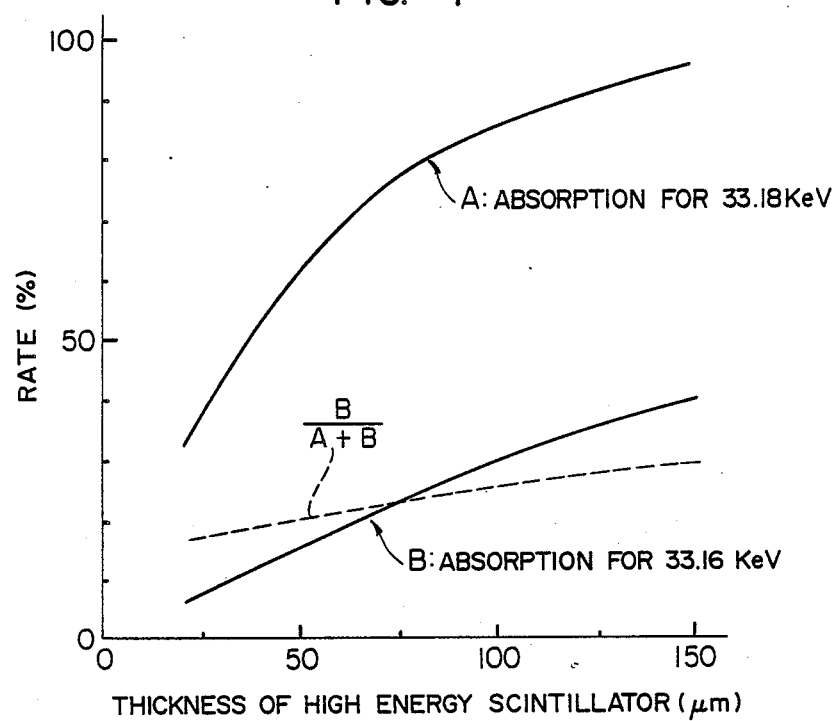
FIG. 4 is a graph showing the absorbance characteristic of the element 4 shown in FIG. 3.

The energy separation capability (resolution) of the energy-sensitive detector will be explained in the case where iodine is used as the contrast agent and an iodinated compound is used as the higher energy scintillator 10. First, the quasi-monochromatic x-ray 2 is assumed to be an x-ray having the bandwidth of several hundreds eV formed by the asymmetric reflection type detector, and the center of the energy bandwidth is set to the absorption edge energy of iodine, 33.17 keV. FIG. 4 shows the absorbances in the higher energy scintillator 10 when such an x-ray is incident there. More specifically, in FIG. 4, A is a curve showing the absorbance for the higher energy component (represented by 33.18 keV) than the absorption edge energy, while B is a curve showing the absorbance for the lower energy component (represented by 33.16 keV) than the absorption edge energy. As seen from the figure, both absorbances are increased with the increase of the thickness of the scintillator, but the ratio (B/A+B) of the absorbance for the lower energy component to the entire absorbance, which is indicated by a dotted line, is about 20% in the range of 20–100 μm of the scintillator thickness. This means that the separation capability, for the higher energy x-ray component in the higher energy scintillator 10 is as high as 80%. Now if the thickness of the higher energy scintillator is 75 μm, 77% of the higher energy x-ray component is absorbed by the higher energy scintillator and the remaining 23% thereof having transmitted through the higher energy scintillator is absorbed by the lower energy scintillator 12 which has a sufficient thickness. Inversely, in connection with the lower energy x-ray component, 23% thereof is absorbed by the higher energy scintillator while the remaining transmitted 77% thereof is absorbed by the lower energy scintillator 12. Thus, the energy separation capability in both scintillators is 77%. This means the presence of the mixed component of 23% in both scintillators. However, the mixed components can be cancelled out through the difference processing between both images formed by the higher and lower x-ray energes so that a final image is not influenced by the mixed components.

Using two-dimensional photo-diode arrays as the photo-detectors 11 and 13, two kinds of x-ray image formed by the higher energy component and the lower energy component than the absorption edge energy of the contrast agent constituting element are converted into electric signals, which are introduced into the data recording and reproducing processor device 7. These image data are processed in the processor device 7 to provide a final image.

Another embodiment of the photodetectors 11 and 13 is to use normal x-ray imaging films. In this embodiment, the images x-rayed on two films are read by a film reader to be converted into electric signals, which are introduced into the data recording and reproducing processor device. Here, the energy-sensitive detector is constituted by two sets of a film used for normal x-raying and an x-ray intensifying screen. More specifically, a first intensifying screen, which is applied with fluorescent material containing the same constituent element as the constituent element of a contrast agent to be injected into a body to be examined, serves as the higher energy scintillator 10. A first photo-sensitive film serving as the photodetector 11 is stacked thereon. A second intensifying screen serving as the lower energy scintillator 12 is stacked thereon. Finally, a second photo-sensitive film serving as the photo-detector 13 is stacked thereon. A light-shielding panel for preventing the mixing of fluorescence intervenes between the above two sets. Further, the detector may be constructed by stacking a first cassette in which the film and intensifying screen for the higher energy detection are located and a second cassette in which the film and intensifying screen for the lower energy detection are located.

Figure 5:
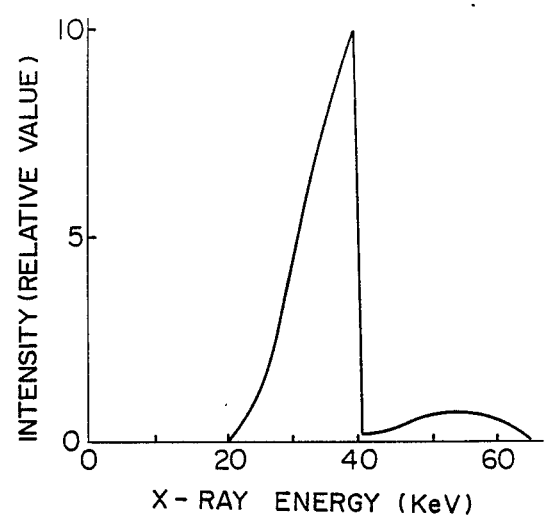
FIG. 5 is a graph showing the spectrum characteristic of an x-ray source in another embodiment according to this invention.

Another embodiment of the x-ray source will be explained. The quasi-monochromatic x-ray 2 may also be provided by an x-ray tube and a filter made of a specific element. For example, when the contrast agent is iodine, the filter may be made of the element having the greater atomic number than iodine. FIG. 5 shows the x-ray spectrum when the filter is made of cerium and the tube voltage is set to 65 kV. Such an x-ray source generally provides the quasi-monochromatic x-ray the energy bandwidth of which is wider than the case of using the synchrotron radiation and the spectroscope, but the resultant effect is similar to the latter case.

In accordance with these embodiments of this invention, a set of images resulting from the energy components very close to and slightly above and below the absorption edge energy of the element constituting a contrast agent can be simultaneously imaged. Thus, the image of only the contrast agent in which any motion artifact or fade due to a body motion is not contained and the soft tissue other than the contrast agent is substantially cancelled can be obtained through the energy subtraction technique.

Since the subtraction image free from the artifact due body motion can be obtained as mentioned above, the above mentioned embodiments can be effectively used for the diagnosis of coronary arteries. Further, the imaging thereof is made possible by injecting the contrast agent from a vein without using an artery catheter. However, since all blood vessels are non-selectively contrasted, also when it is desired that the coronary artery is visualized, the images of blood in venticles, great blood vessels, lung blood vessels, etc. are superposed on the resultant subtraction energy images. On the other hand, the coronary artery has many branches which are, as a whole, three-dimensionally distributed so as to wrap a heart. In order to three-dimensionally visualize the entire blood vessel system having such a three-dimensional structure, a stereo imaging can be effectively used. The stereo imaging, which provides depth information, makes easy the distinction of the coronary artery. It also can distinguish the orientations of the respective branches of the coronary artery, thus accurately finding the location of a pathological change.

Figure 6:
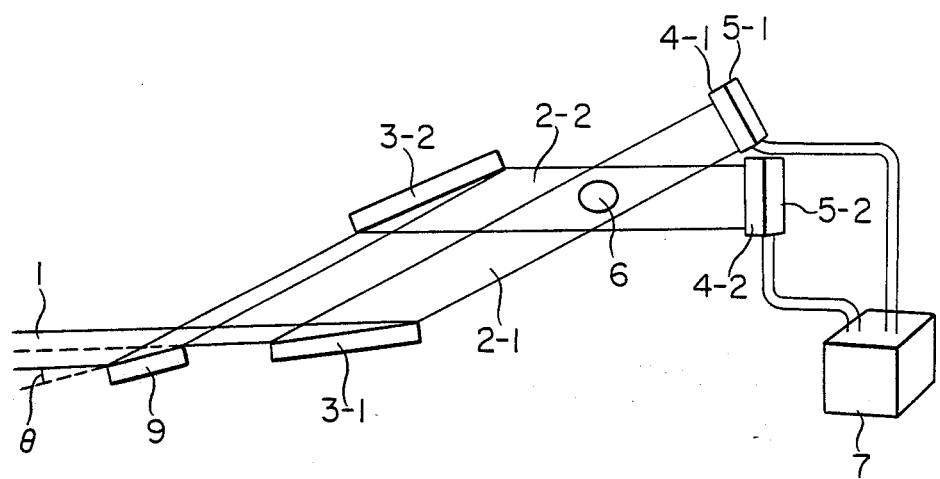
FIG. 6 is a block diagram of still another embodiment according to this invention.

FIG. 6. shows an embodiment of the stereo imaging. An incident synchrotron radiation beam 1 is flat in its section, narrower in the paper surface direction and wider in the direction perpendicular thereto. A single crystal 9 is a beam splitter crystal.

The lower half of the beam 1 is incident to the beam splitter while the remaining upper half thereof passes the beam splitter without being incident thereto.

The single crystal 9 has a diffraction lattice plane. Thus, only the x-ray at the energy having the relation, $E=12.4/(2d.\sin\theta)$ (E is expressed in keV, and d which is the distance between crystal lattices is expressed in Å) to the x-ray incident at the angle $\theta$ with the diffraction crystal face reflects according to the theory of the Bragg reflection. The reflected beam deviates by $2\theta$ from the direction of the incident beam. In this way, the beam 1 is split into two components by the beam splitter crystal 9.

A single crystal 3-1 is a crystal for asymmetric reflection as shown in FIG. 2, which has the surface cut out at an angle $\theta_2$ with the diffraction lattice plane.

The x-ray incident to the single crystal 3-1 is asymmetrical reflected there to provide are quasi-monochromatic x-ray beam 2-1. On the other hand, a single crystal 3-2, which is also the crystal for asymmetric reflection, reflects the x-ray beam reflected from the single crystal 9 to provide a quasi-monochromatic x-ray beam 2-2 in the direction different from that of 2-1. The quasi-monochromatic x-ray beams 2-1 and 2-2 are incident to a body to be examined at different angles. The x-ray beams having been transmitted through the body are detected by two sets of energy-sensitive detectors 4-1, 5-1 and 4-2, 5-2, such as shown in FIG. 3. In the data recording and reproducing processor device 7, a first energy subtraction image is obtained from the data taken from the detector 4-1, 5-1 while dasecond energy subtraction image is obtained from the data taken the detector 4-2, 5-2. By displaying in parallel these images which have been imaged at the same time, the body can be stereoscopically observed. Further, by displaying a superposition of both images, a stereoscopic image or an image with the image at a specific depth emphasized can be obtained.

We claim:

1. A spectral type radiation imaging system in which x-ray imaging is performed using a contrast agent, comprising:
   an x-ray source for emitting a quasi-monochromatic x-ray beam to be projected to an object, the energy bandwidth of which extends between, above and below the absorption edge energy of an element constituting the contrast agent, wherein said x-ray source comprises as asymmetrically cut crystal for asymmetrically reflecting an incident x-ray beam to provide the quasi-monochromatic x-ray beam;
   a first x-ray detector for detecting x-rays penetrating through the object, said first x-ray detector comprising a scintillator made of fluorescent material containing the contrast-agent constituting element; and
   a second x-ray detector, at a location behind the first x-ray detector so that the first x-ray detector is interposed between the x-ray source and second x-ray detector, for detecting x-rays penetrating through said first x-ray detector.

2. A spectral type radiation imaging system according to claim 1, further comprising data processing means for performing subtraction between output data of said first and second x-ray detectors.

3. A spectral type radiation imaging system according to claim 1, wherein said contrast agent is iodine, and the scintillator is made of an iodine compound.

4. A spectral type radiation imaging system according to claim 3, wherein said iodide compound is cesium iodide or sodium iodide.

5. A spectral type radiation imaging system according to claim 1, wherein said contrast agent is barium, and the scintillator is made of a barium compound.

6. A spectral type radiation imaging system according to claim 5, wherein said barium compound is a barium halide.

7. A spectral type radiation imaging system according to claim 1, wherein each of the first and second x-ray detectors includes a photodetector, respectively adjacent said scintillator and another scintillator, said another scintillator being included in the second x-ray detector.

8. A spectral type radiation imaging system according to claim 7, wherein each of the photodetectors include a photo sensitive film, the first and second x-ray detectors forming a stack of said scintillator, a first photosensitive film, said another scintillator and a second photosensitive film, in sequence.

9. A spectral type radiation imaging system according to claim 8, wherein a light-shielding panel is provide between the first photosensitive film and said another scintillator.

10. A spectral type radiation imaging system according to claim 8, wherein the first and second photosensitive films are x-ray imaging films.

11. A spectral type radiation imaging system according to claim 1, further comprising a second source of x-rays, and third and fourth x-rays detectors, the second source of x-rays providing a second quasi-monochromatic x-ray beam, to be projected to the object in a direction different than the direction of said quasi-monochromatic x-ray beam emitted from said x-rays source, the third and fourth x-ray detectors detecting relatively higher and lower energy components of said second quasi-monochromatic x-ray beam penetrating through the object, whereby a stereoscopic image of the object can be achieved.

12. A spectral type radiation imaging system according to claim 1, wherein the center of said energy bandwidth of said x-ray source is coincident to said absorption edge energy.

13. A spectral type radiation imaging system according to claim 1, wherein said x-rays source includes an x-ray tube and a filter constituted by an element having a greater atomic number than said contrast-agent constituting element.

14. A spectral type radiation imaging system according to claim 13, wherein said filter constituting element is cerium, and said contrast-agent constituting element is iodine.

* * * * *